United States Patent [19]

Newkirk et al.

[11] 4,199,647
[45] Apr. 22, 1980

[54] FIBER LUBRICANTS DERIVED FROM POLYETHOXYLATED AND POLYOXYALKYLATED REACTION PRODUCTS OF AN ALPHA-OLEFIN EPOXIDE AND A FATTY ALCOHOL

[75] Inventors: David D. Newkirk; Robert B. Login, both of Woodhaven, Mich.

[73] Assignee: BASF Wyandotte Corporation, Wyandotte, Mich.

[21] Appl. No.: 856,047

[22] Filed: Nov. 30, 1977

[51] Int. Cl.² .............. C07C 43/00; C07C 43/04; D06M 3/38; D06M 5/08; D06M 15/10
[52] U.S. Cl. .............. 428/394; 252/8.9; 568/613
[58] Field of Search ............ 260/615 B; 252/8.9; 428/395, 392, 394

[56] References Cited
U.S. PATENT DOCUMENTS

| | | | |
|---|---|---|---|
| 2,620,304 | 12/1952 | Stewart et al. | 252/8.9 |
| 2,690,426 | 9/1954 | Jefferson et al. | 252/8.9 |
| 2,932,670 | 4/1960 | Blake | 260/615 B |
| 3,676,199 | 7/1972 | Hewitt et al. | 252/8.9 |
| 3,708,364 | 1/1973 | Kalopissis | 260/615 B |
| 3,943,178 | 3/1976 | Stein et al. | 252/8.9 |
| 3,963,628 | 6/1976 | Park | 252/8.9 |

*Primary Examiner*—J. C. Cannon
*Attorney, Agent, or Firm*—Andrew E. Pierce

[57] ABSTRACT

Lubricants and processing aids for thermoplastic synthetic fibers, particularly polyester and nylon fibers are disclosed together with processes therefor. Said lubricants comprise compounds having the structural formula:

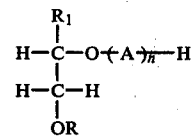

in which R and $R_1$ are independently selected from straight or branched chain aliphatic radicals having about 7 to about 22 carbon atoms; A is oxyethylene or a heteric mixture of oxyethylene and oxypropylene residues derived from the reaction of ethylene oxide and 1,2-propylene oxide in the respective ratio by weight of about 3:7 to about 9:1; and n has a value to produce a compound having a molecular weight of about 300 to about 3000. Said compounds are the ethoxylated or alkoxylated reaction product of the reaction product of an alpha-olefin epoxide and a fatty alcohol. Where liquid products are desired which contain the higher numbered carbon chain residues, low viscosity compounds can be obtained by oxyalkylating the intermediate obtained by reacting an alpha-olefin epoxide with a fatty alcohol using an ethylene oxide and 1,2-propylene oxide mixture in the respective ratio as set forth above. By properly balancing the carbon chain length of the R and $R_1$ groups in the lubricant compounds with the oxyethylene or oxyalkylene ratio, variation between insoluble and soluble products can be obtained.

5 Claims, No Drawings

FIBER LUBRICANTS DERIVED FROM POLYETHOXYLATED AND POLYOXYALKYLATED REACTION PRODUCTS OF AN ALPHA-OLEFIN EPOXIDE AND A FATTY ALCOHOL

BACKGROUND OF THE INVENTION

1. Field of the Invention

This invention relates to the false twist processing of synthetic fibers, particularly polyester and nylon fibers with fiber processing aids applied as spin-finishes subsequent to extrusion of the fibers from the spinneret.

2. Description of the Prior Art

In the production of polyester and polyamide filament, the addition of a chemical coating after extrusion from the spinneret is essential in order to process the emerging filaments into fibers. It is known to utilize, as fiber lubricant components, polyoxyethylenes and heteric polyoxyalkylenes derived from ethylene oxide and 1,2-propylene oxide derivatives of fatty acids and fatty alcohols. Such compounds often consist of long chain alkyl groups with attached polyoxyalkylene chains; the fatty acid or fatty alcohol residues providing lubricity as a consequence of their structural similarity to mineral lubricating oils and the polyoxyalkylene residues providing wetting of the fiber surface and water solubility. It is known to obtain lubricants derived from the oxyalkylation of diols, monols and fatty acids by utilizing a heteric mixture of oxyethylene and oxypropylene groups in the molecule of the fiber lubricant in accordance with U.S. Pat. No. 2,457,139 and U.S. Pat. No. 2,425,755. It is also known to produce lubricants for multi-filament polyester yarns by the heteric oxyalkylation of an initiator compound using ethylene oxide and 1,2-propylene oxide wherein said initiator is a fatty acid having 6 to 18 carbon atoms in the alkyl chain. Similar fiber lubricating compositions are disclosed in British Pat. No. 1,460,960 wherein fiber lubricants are produced by the heteric oxyalkylation of a fatty acid having 7 to 21 carbon atoms in the alkyl chain.

SUMMARY OF THE INVENTION

It is a primary object of this invention to provide fiber lubricating compounds, or processing aids, useful as coatings for synthetic fibers such as polyester or nylon fibers. A balanced blend of lubricity and water-dispersibility, or water-solubility, can be obtained in the compounds of the invention, certain embodiments of which are low viscosity liquids at room temperature. Thus certain lubricant compounds of the invention can be applied to fibers to produce lubricated fibers, if desired, without dilution in water since certain embodiments of the lubricants of the invention have suitably low viscosities at ambient temperature as compared to conventional compounds of the prior art. In addition, certain of the lubricant compounds of the invention exhibit the characteristic of self-emulsification and others exhibit the characteristic of water-solubility at ambient temperature thus allowing application of these lubricants to textile fibers by utilizing aqueous dispersions, emulsions or solutions of the lubricant compounds.

These and other objects are accomplished in accordance with this invention by utilizing lubricant compounds derived from an intermediate compound obtained by the reaction of one mole of a straight or branched chain alpha-olefin epoxide with one mole of a fatty alcohol having a straight or branched chain. Such intermediates have the structural formula:

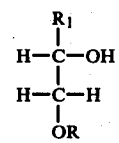

wherein $R_1$ is derived from the residue of a straight or branched chain alpha-olefin epoxide and R is derived from the residue of a straight or branched chain fatty alcohol and have the same definition as hereinbefore given. These intermediates contain a hydroxyl group in the center of the molecule which is reactive in an oxyalkylation reaction.

Upon oxyalkylation such as with either (1) ethylene oxide or (2) a mixture of ethylene oxide and 1,2-propylene oxide so as to obtain a polyoxyalkylated chain which is characterized as heteric in nature, the following compounds are obtained:

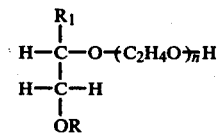

and

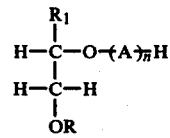

wherein R and $R_1$ are independently selected from straight or branched chain aliphatic radicals having about 7 to about 22 carbon atoms; A is a mixture of oxyethylene and oxypropylene residues derived from the reaction of ethylene oxide and 1,2-propylene oxide in the respective ratio by weight of about 3:7 to about 9:1, and n has a value to produce a compound having a molecular weight of about 300 to about 3000, preferably about 450 to about 1500, and most preferably about 600 to about 1200.

The lubricant compositions of the invention comprising oxyalkylated compounds as indicated above are characterized by a balanced blend of lubricity and wetting ability derived from the fact that the hydrophile oxyalkylene groups are attached to the center of the hydrophobic portion of the molecule.

DETAILED DESCRIPTION OF THE INVENTION AND OF THE PREFERRED EMBODIMENTS

The lubricant compounds of the invention provide a novel fiber lubricant which overcomes certain of the difficulties generally associated with textile fiber lubricants. For instance, where mineral oil or a fatty acid ester such as butyl stearate is utilized alone or in combination with other components as a fiber lubricant, such compositions are difficult to apply to the fiber since the compositions require the use of an emulsifier such as a nonionic or anionic wetting agent and there is a tendency toward non-uniformity of the application of the fiber lubricant to the fiber under these circumstances. In addition, such compositions utilizing mineral oil or fatty acid esters are not easily biodegraded since they usually contain branching and also represent a pollution problem in the sense that oil film or sludge is discharged into surrounding rivers and waterways adjacent to the textile factory where such lubricants are utilized.

Where the prior art fiber lubricant consists of a polyoxyalkylated branched chain fatty alcohol or fatty acid, it is possible to provide self-emulsifying or water soluble lubricating compositions, so that the appearance of rivers or surrounding waterways contaminated with such compounds is not seriously affected. Nevertheless these compounds which include secondary or tertiary carbon in the molecule are not readily subject to biodegradation.

Another drawback of certain of the prior art lubricants is that it is difficult to incorporate the higher fatty acid or alcohols in the fiber lubricant compound and yet obtain compounds having low viscosity which will permit ease of application to the textile fiber as well as an improved lubricating effect. The compounds of the invention overcome this disadvantage since such compounds can be either oxyethylated with a relatively small amount of ethylene oxide or oxyalkylated utilizing a mixture of ethylene oxide and 1,2-propylene oxide. The mixture of ethylene oxide and 1,2-propylene oxide can be employed in a ratio so as to maintain the proper balance in the compound between the water-solubility or self-emulsification characteristics and low viscosity at ambient temperature.

The fiber lubricants of the invention are obtained by preparing an intermediate which is produced by reacting a straight or branched chain alpha-olefin epoxide with a straight or branched chain fatty alcohol. The intermediate contains a single ether group. A single hydroxyl group is located in the center of the intermediate molecule on either side of which there are attached straight or branched alkyl chains derived from the residue of the alpha-olefin epoxide and the residue of the fatty alcohol. The fatty alcohol is first reacted to produce the alkoxide at elevated temperature in the presence of an alkali such as an alkali metal hydroxide, i.e., sodium, lithium, and potassium hydroxide. The alkoxide is then reacted with an alpha-olefin epoxide to produce the hydroxyl group-containing monoether intermediate of the invention which is in turn ethoxylated or alkoxylated for instance with ethylene oxide and propylene oxide to produce a lubricant compound of the desired molecular weight. The fatty alcohol utilized alone or in blends generally contains about 7 to about 22 carbon atoms preferably about 10 to about 18 carbon atoms and most preferably about 12 to about 15 carbon atoms in the aliphatic chain. Blends of these alcohols are preferred because of their commercial availability. Representative fatty alcohols having about 7 to about 22 carbon atoms in the aliphatic chain are the primary, secondary, and tertiary alcohols such as octyl alcohol, methyl isobutyl carbinol, decyl alcohol, cetyl alcohol, 2-ethyl hexanol, heptanol, nonanol, undecanol, dodecanol, tridecanol, pentadecanol, hexadecanol, heptadecanol, stearyl alcohol, arachidic alcohol, 1-docosanol, 5-methyl 5-dodecanol, and 4-ethyl 4-dodecanol.

The fatty alcohols are available commercially as mixtures of fatty alcohols such as a mixture of fatty alcohols having carbon chain lengths ranging from about 12 to about 15 as represented by the commercially available product sold under the trademark "NEODOL" 25 or the fatty alcohol blend sold under the trademark "EPAL" 12/85 which is a mixture of fatty alcohols in which the fatty alcohol having a 12 carbon chain predominates to the extent of 85 percent.

The straight or branched chain alpha-olefin epoxides utilized alone or in blends to prepare the intermediate compounds of the invention have about 7 to about 22 carbon atoms, preferably about 10 to about 18 carbon atoms, and most preferably about 12 to about 15 carbon atoms. Most often the alpha-olefin epoxides are commercially available as blends of various chain length alpha-olefin epoxides, for instance, a commercially available alpha-olefin epoxide of 1-tetradecene is sold under the trademark "VIKOLOX" 14.

The alkylene oxides, which can be employed in the preparation of the fiber lubricants of the present invention generally include in addition to ethylene oxide and propylene oxide, the isomeric normal butylene oxides, hexylene oxide, octalene oxide, dodecene oxide, and ethoxy and other alkoxy propylene oxides. Preferably ethylene oxide or a mixture of ethylene oxide and 1,2-propylene oxide is used in preparing the fiber lubricants of the invention. Generally the oxyalkylation reaction can be either base or acid catalyzed and preferably such reaction is base catalyzed. The proportions of ethylene oxide to 1,2-propylene oxide which are utilized in order to insure that the product obtained is a liquid at ambient temperatures are respectively in the ratio of about 3:7 to about 9:1. The oxyethylation or oxyalkylation of the intermediate compounds of the invention is continued until the polymer compound produced has a molecular weight of about 300 to about 3000, preferably about 450 to about 1500, and most preferably about 600 to about 1200. The conditions for the oxyalkylation reaction and the catalyst used therein are conventional and known to those skilled in the art. Generally, reaction temperatures of 110° C. to 150° C., reaction pressures of atomospheric to 150 psig, and reaction times of 2 hours to 24 hours are employed.

Representative and illustrative fiber lubricants of the invention are the ethoxylated reaction product of 4 moles of ethylene oxide and the reaction product of an alpha-olefin epoxide blend having a mixture of 14 to 16 carbon chain alpha-olefin epoxides and a fatty alcohol consisting of a mixture of fatty alcohols having carbon chain lengths between 12 and 15 carbons; the fiber lubricant produced by ethoxylating with 7.4 moles of ethylene oxide the reaction product of an alpha-olefin epoxide blend of $C_{14}$ to $C_{16}$ chain length alpha-olefin epoxides with a fatty alcohol blend containing 85 percent of the 12 carbon fatty alcohol; a fiber lubricant prepared by ethoxylating with 11 moles of ethylene oxide the reaction product of a $C_{14}$ to $C_{16}$ alpha-olefin epoxide blend with a fatty alcohol blend containing 85 percent $C_{12}$ fatty alcohol; and a heteric alkoxylated fiber lubricant prepared by alkoxylating the reaction product of a $C_{14}$ to $C_{16}$ alpha-olefin epoxide blend with a fatty alcohol blend containing 85 percent $C_{12}$ fatty alcohol with a mixture of 12 moles of ethylene oxide and 2 moles of 1,2-propylene oxide.

The compounds of the invention containing polyoxyalkylene chains in the molecule are unique fiber lubricants in which the polyoxyalkylene chains are attached to the hydrophobe in the center of the molecule. Generally such type structures are believed more readily biodegradable than prior art alkoxylated fatty acid and alcohol compounds. The former can be attacked by bacteria on both ends of the chain of the hydrophobe rather than on only one end of the chain thus eventually breaking up the polymer into smaller components at a faster rate. The lubricants of the invention are preferably derived from straight chain fatty alcohols and straight chain alpha-olefin epoxides where optimum biodegradability is desired.

In general, the fiber lubricants of the invention exhibit a desirable balance of properties including self-emulsifiability in water together with low viscosity at ambient temperature. The preferred products are generally fluids at ambient temperature. The fiber lubricants of the invention can be easily prepared so as to contain 2 straight chain aliphatic residues from the straight chain alpha-olefin epoxide and fatty alcohol instead of one as in the prior art polyalkyoxylated fatty alcohol and fatty acid fiber lubricants derived from straight chain fatty alcohols or fatty acids. Thus the straight chain fiber lubricants of the invention are believed to be more easily biodegradable.

The low viscosity of certain embodiments of the fiber lubricants of the invention make it possible to apply them to the fibers without dilution by passing the fibers through a trough or having the fibers make contact with a "kiss" roll rotating in a trough in which the fiber lubricants are contained. The fiber lubricants of the invention can also be applied to the fibers as an aqueous dispersion or solution. Generally about 0.05% by weight to about 2% by weight, preferably about 0.1% by weight to about 1.5% by weight, of the fiber lubricants of the invention are applied to the thermoplastic synthetic fibers based upon the weight of said fibers.

The water-solubility or water-dispersibility of the fiber lubricants of the invention also facilitates the subsequent scouring operation utilized to remove the lubricant subsequent to the mechanical and heat treatment of the yarn prior to the dyeing operation. In addition the properties of water-solubility or self-emulsifiability to form aqueous dispersions of the fiber lubricants of the invention aid in disposal of these materials by the textile mill usually preventing the accumulation of an oil film or slick in nearby streams or ponds as would be the case with a mineral oil-based fiber lubricant of the prior art. While the high molecular weight branched chain prior art mineral oil type fiber lubricants would be very slowly decomposed by bacteria subsequent to disposal, the nature of the fiber lubricants of the invention, especially where straight chain reactants are utilized, permit biodegradation to take place readily.

The fiber lubricants of the invention have excellent stability to smoking under conditions of use at elevated temperature in the mechanical and heat treatment operation subsequent to extrusion of the fiber, as compared to prior art ethoxylated and alkoxylated fatty acids and fatty alcohols as well as mineral oils utilized in the prior art. Additional high temperature stability of the fiber lubricants of the invention can be obtained by the addition of conventional stabilizers and anti-oxidants as is known in the art.

The following test methods were used in evaluating the lubricity of the fiber lubricants of the instant invention. Lubricity of polyester filament yarn having fiber lubricants of the invention applied thereto was evaluated by applying to a scoured 125-denier, partially-oriented polyester filament commercial yarn the desired percentage of lubricant. The lubricant was applied to the yarn utilizing an Atlas Yarn Finish Applicator made by the Precision Machine Development Company in which yarn is passed at a controlled speed through a continually replenished drop of finish solution of specified strength in order to achieve a uniform wetting of the yarn. The solution is metered using a syringe pump. The yarn during treatment passes from a feeder globule over an adjustable canter roller which functions to space the yarn filaments for passage over a drying drum utilized in conjunction with the application of heat to remove the water applied to the yarn in the application of the fiber lubricant to the yarn. The yarn finally passes over a winding tube and is subsequently conditioned overnight under controlled conditions of temperature and humidity (65 percent relative humidity and 70 degrees Fahrenheit) before being tested. Utilizing the fiber lubricant treated yarn, the coefficient of friction (f) was determined using a Rothschild F-Meter in which the yarn is passed over a 0.313 inch diameter satin chrome pin at a contact angle of 180 degrees and at a speed of 50, 100, 150, 200, 250 and, wherever possible, 300 meters per minute. Tensiometers on the Rothschild machine measure the yarn tension before and after it passes over the friction pin so as to insure uniformity of conditions. The input tension is maintained at a value of 12 grams by use of a controlling drum. The coefficient of friction is determined directly from the instrument chart. For comparison, the polyester filament yarn is measured for lubricity prior to treatment with the fiber lubricant of the invention and after being treated with prior art lubricants. Test results are shown in the following Table.

Table

Coefficient of Friction of Lubricant on 125 Denier Polyester Yarn

| Lubricant (% by weight on yarn) | Speed (meters/min) | Coefficient of Friction (f) |
|---|---|---|
| Example 3, 1% | 50 | 0.80 |
| | 100 | 0.85 |
| | 150 | 0.90 |
| | 200 | 0.90 |
| | 300 | 0.93 |
| No lubricant | 50 | (greater than |
| | 100 | 1.0; yarn breaks) |
| | 300 | |
| Example 5, 1.6% | 50 | 0.80 |
| | 100 | 0.87 |
| | 150 | 0.91 |
| | 200 | 0.91 |
| | 300 | 0.91 |

The following examples illustrate the various aspects of the invention but are not intended to limit it. Where not otherwise specified throughout the specification and claims, temperatures are given in degrees centigrade and parts, percentages and proportions are by weight.

EXAMPLE 1

This example illustrates the general procedure for obtaining the fiber lubricant compounds of the invention. Generally the reaction is in two steps. In step one, one mole of an alpha-olefin epoxide is reacted with one mole of a fatty alcohol to produce an intermediate which is thereafter reacted in step two with either ethylene oxide or a mixture of ethylene oxide and 1,2-propylene oxide to obtain the desired molecular weight.

An intermediate was prepared by adding to a 5-liter, 4-neck flask equipped with stirring means, distilling heat and temperature control means, 1401 grams (7.5 moles) of a straight chain fatty alcohol blend containing 85 percent $C_{12}$ fatty alcohol and sold under the trademark "EPAL" 12/85. This fatty alcohol contains 85 percent 1-hydroxydodecane. There was then added 19.4 grams of sodium methoxide to the fatty alcohol, the mixture was stripped for one hour at 75° centigrade. The temperature was then raised to 135° centigrade and 1600 grams (7.5 moles) of a straight chain alpha-olefin epoxide containing a mixture of $C_{14}$ to $C_{16}$ alpha-olefin epoxide and consisting substantially of the alpha-olefin epoxide of 1-tetradecene sold under the trademark "VIKOLOX" 14 was added to the flask over a six hour period. Heating was continued and the temperature allowed to slowly increase from 136° centigrade to 154° centigrade over a three hour period. The product was stripped for three hours at 152° centigrade using a vacuum of 2 millimeters of mercury. The intermediate product had a hydroxyl number of 126 and 0.06 percent oxirane oxygen.

Using the intermediate product prepared above, 650 grams of this product was added to a one gallon autoclave together with 5 grams of 90 percent flake potassium hydroxide and the mixture heated to 135° centigrade and then stripped for 30 minutes at a vacuum of 2 millimeters of mercury. The autoclave was then pressurized to 34 pounds per square inch gauge with nitrogen and 530 grams of ethylene oxide was added to the autoclave over a period of 2.5 hours. After an additional reaction time of one hour, the reaction was considered complete and the product was stripped to remove volatiles followed by deionization. The product obtained had a hydroxyl number of 69.7, a molecular weight of 838, a viscosity (Brookfield) at 25° centigrade of 820 centipoise, and was found to form a stable 25 percent by weight solids emulsion in water.

EXAMPLE 2

Following the procedure of Example 1 the intermediate prepared therein was ethoxylated utilizing 11 moles of ethylene oxide. The product obtained had a hydroxyl number of 57.9, a molecular weight of 968, and a smoke point of 187° centigrade.

EXAMPLE 3

Following the general procedure of Example 1, the intermediate prepared therein was alkoxylated with a mixture of 12 moles of ethylene oxide and 2 moles of 1,2-propylene oxide to produce a heteric alkoxylated reaction product of an alpha-olefin epoxide and a fatty alcohol. The product obtained had a hydroxyl number of 49.1, a surface tension of 43.5 dynes per centimeter, a viscosity (Brookfield) of 160 centipoise, a smoke point of 181° centigrade, and a molecular weight of 1140.

EXAMPLE 4

Following the general procedure of Example 1, an intermediate compound was prepared by reacting a straight chain alpha-olefin epoxide blend sold under the trademark "VIKOLOX" 14 with a fatty alcohol blend of $C_{12}$ to $C_{15}$ fatty alcohols sold under the trademark "NEODOL" 25. The intermediate was ethoxylated following the general procedure of Example 1 by reacting 1300 grams (3 moles) of the intermediate with 680 grams (12 moles) of ethylene oxide. The product obtained had a hydroxyl number of 90.5 to 98.8, an oxirane oxygen of 0.05 to 0.07, a surface tension (0.1 percent by weight aqueous solution) of 29.5 dynes per centimeter, a viscosity (Brookfield) at 25° centigrade of 60 centipoise, and a molecular weight of 560–620.

EXAMPLE 5

(Control—forming no part of this invention)

A fatty alcohol alkoxylate of the prior art was prepared by alkoxylating, using base catalysis, a blend of $C_{13}$–$C_{15}$ straight chain fatty alcohols with a 30:70 molar ratio respectively of a mixture of ethylene oxide and propylene oxide using methods known in the prior art. A heteric alkoxylate was obtained having a molecular weight of about 1300.

While this invention has been described with reference to certain specific embodiments, it will be recognized by those skilled in the art that many variations are possible without departing from the spirit and scope of the invention and it will be understood that it is intended to cover all changes and modifications of the invention disclosed herein for the purposes of illustration which do not constitute departures from the spirit and scope of the invention.

The embodiments of the invention in which an exclusive property or privilege is claimed are defined as follows:

1. The process of lubricating thermoplastic synthetic fibers comprising the application to said fibers of a composition comprising a compound having the structural formula:

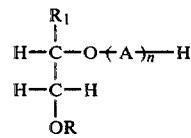

wherein R and $R_1$ are independently selected from straight or branched chain aliphatic radicals having about 7 to about 22 carbon atoms; A is oxyethylene or a heteric mixture of oxyethylene and oxypropylene residues derived from the reaction of ethylene oxide and 1,2-propylene oxide in the respective ratio by weight of 3:7 to 9:1, and n has a value to produce said compound having a molecular weight of about 300 to about 3000.

2. The process of lubricating thermoplastic, synthetic fibers comprising the application to said fibers of a composition comprising a compound having the structural formula:

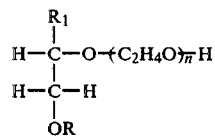

said compound being the ethoxylated reaction product of the reaction product of an alpha-olefin epoxide and a fatty alcohol wherein R and $R_1$ are independently selected from straight or branched chain aliphatic radicals having about 7 to about 22 carbon atoms and n has a value to produce a compound having a molecular weight of about 300 to about 3000.

3. A lubricated, thermoplastic, synthetic fiber comprising a polyester or nylon fiber having incorporated thereon a lubricating composition comprising a lubricating compound having the structural formula:

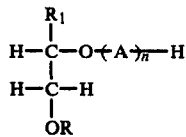

wherein R and $R_1$ are independently selected from straight or branched chain aliphatic radicals having about 7 to about 22 carbon atoms; A is oxyethylene or a heteric mixture of oxyethylene and oxypropylene residues derived from the reaction of ethylene oxide and 1,2-propylene oxide in the respective ratio by weight of 3:7 to 9:1, and n has a value to produce said compound having a molecular weight of about 300 to about 3000.

4. A lubricated thermoplastic, synthetic fiber comprising a polyester or nylon fiber having incorporated thereon a lubricating composition comprising a compound having the structural formula:

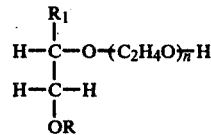

said compound being the ethoxylated reaction product of the reaction product of an alpha-olefin epoxide and a fatty alcohol wherein R and $R_1$ are independently selected from straight or branched chain aliphatic radicals having about 7 to about 22 carbon atoms and n has a value to produce said compound having a molecular weight of about 300 to about 3000.

5. The lubricated polyester fiber of claim 4 having applied thereto about 0.05 percent by weight to about 2 percent by weight of said composition based upon the weight of said fiber.

* * * * *